United States Patent
Michalczak et al.

(10) Patent No.: US 8,816,125 B2
(45) Date of Patent: Aug. 26, 2014

(54) PROCESS FOR THE CONTINUOUS PREPARATION OF (CYCLO)ALIPHATIC DIISOCYANATES

(75) Inventors: Hans-Werner Michalczak, Herne (DE); Stephan Kohlstruk, Duelmen (DE); Manfred Kreczinski, Herne (DE); Gerda Grund, Coesfeld (DE); Rainer Lomoelder, Muenster (DE)

(73) Assignee: Evonik Degussa GmbH, Essen (DE)

( * ) Notice: Subject to any disclaimer, the term of this patent is extended or adjusted under 35 U.S.C. 154(b) by 689 days.

(21) Appl. No.: 12/519,795

(22) PCT Filed: Nov. 5, 2007

(86) PCT No.: PCT/EP2007/061870
§ 371 (c)(1),
(2), (4) Date: Jun. 18, 2009

(87) PCT Pub. No.: WO2008/077672
PCT Pub. Date: Jul. 3, 2008

(65) Prior Publication Data
US 2010/0036154 A1    Feb. 11, 2010

(30) Foreign Application Priority Data
Dec. 23, 2006  (DE) .................. 10 2006 061 475

(51) Int. Cl.
C07C 263/00 (2006.01)
C07C 263/04 (2006.01)
C07C 269/04 (2006.01)

(52) U.S. Cl.
CPC ............ C07C 263/04 (2013.01); C07C 269/04 (2013.01); C07C 2101/14 (2013.01)
USPC ........................................ 560/344

(58) Field of Classification Search
CPC .. C07C 263/04; C07C 265/14; C07C 263/06; C07C 269/00
See application file for complete search history.

(56) References Cited

U.S. PATENT DOCUMENTS

| | | | |
|---|---|---|---|
| 3,378,584 A * | 4/1968 | Hollowell | ................. 564/73 |
| 4,204,053 A | 5/1980 | Elstrom et al. | |
| 5,087,739 A | 2/1992 | Bohmholdt et al. | |
| 5,207,942 A * | 5/1993 | Scherzer et al. | ............ 252/182.2 |
| 5,360,931 A | 11/1994 | Bohmholdt et al. | |
| 7,307,186 B2 | 12/2007 | Kohlstruk et al. | |
| 7,329,776 B2 | 2/2008 | Kohlstruk et al. | |
| 7,339,074 B2 | 3/2008 | Kohlstruk et al. | |
| 7,371,891 B2 | 5/2008 | Kohlstruk et al. | |
| 7,420,080 B2 | 9/2008 | Kohlstruk et al. | |
| 2005/0250960 A1 | 11/2005 | Kohlstruk et al. | |
| 2006/0025626 A1 | 2/2006 | Kohlstruk et al. | |
| 2010/0168329 A1 | 7/2010 | Hoppe et al. | |

FOREIGN PATENT DOCUMENTS

| | | |
|---|---|---|
| DE | 28 36 511 | 3/1979 |
| EP | 0 355 443 | 2/1990 |
| EP | 1 634 868 | 3/2006 |

OTHER PUBLICATIONS

Columbia Nitrogen Corp. Urea Product Data Sheet, Nov. 1988.*
PotashCorp Urea MSDS, Apr. 2006.*
PotashCorp Urea Products Use Information, retrieved from PotashCorp's website Nov. 2011.*
Schwetlick et al., J. Chem. Soc. Perkin Trans. 2 (1995), 395.*
Iwakura et al., J. Polymer Science Part A-1 (1968), 6, 1087.*
U.S. Appl. No. 07/386,223, filed Jul. 28, 1999, Bohmholdt et al.
U.S. Appl. No. 11/100,603, filed Apr. 7, 2005, Kohlstruk et al.
U.S. Appl. No. 13/516,457, filed Jul. 27, 2012, Hoppe et al.
U.S. Appl. No. 11/720,812, filed Jun. 4, 2007, Hoppe et al.

* cited by examiner

*Primary Examiner* — Fereydoun G Sajjadi
*Assistant Examiner* — Jennifer C Sawyer
(74) *Attorney, Agent, or Firm* — Oblon, Spivak, McClelland, Maier & Neustadt, L.L.P.

(57) ABSTRACT

The invention relates to a multi-stage process for the continuous, phosgene-free preparation of (cyclo)aliphatic diisocyanates that comprises the conversion of (cyclo)aliphatic diamines into the corresponding (cyclo)alkylene biscarbamates and the thermal cleaving of the latter into the (cyclo)alkylene diisocyanates and alcohol. The urea used in accordance with the invention and also the urea employed for the preparation of urea equivalents (e.g. alkyl carbonates, alkyl carbamates) as a possible precursor for the synthesis of the (cyclo)aliphatic biscarbamates is unconditioned.

14 Claims, No Drawings

PROCESS FOR THE CONTINUOUS PREPARATION OF (CYCLO)ALIPHATIC DIISOCYANATES

The invention relates to a multistage process for continuous phosgene-free preparation of (cyclo)aliphatic diisocyanates, which comprises the conversion of (cyclo)aliphatic diamines to the corresponding (cyclo)alkylene biscarbamates and the thermal cleavage of the latter to the (cyclo)alkylene diisocyanates and alcohol.

Diisocyanates are valuable chemical compounds which, by the principle of the diisocyanate polyaddition process, allow the controlled formation of polymers which find various industrial uses as polycarbamates or polyureas in foams, elastomers, thermoplastics, fibers, light-stable polycarbamate coatings or adhesives.

The synthetic access route to isocyanates may be via a series of different routes. The oldest variant for industrial scale preparation of isocyanates, which is still prevalent today, is the phosgenation of the corresponding amines using corrosive, very toxic phosgene which contains a high proportion of chlorine, which places particularly high demands on its handling on the industrial scale.

There are several methods for avoiding the use of phosgene for preparation of isocyanates in industrial orders of magnitude. The term "phosgene-free process" is frequently used in connection with the conversion of amines to isocyanates using alternative carbonylating agents, e.g. urea or dialkyl carbonate (EP 18 586, EP 355 443, U.S. Pat. No. 4,268,683, EP 990 644).

The so-called urea route is based on the urea-mediated conversion of diamines to diisocyanates via a two-stage process. In the first process step, a diamine is reacted with alcohol in the presence of urea or urea equivalents (e.g. alkyl carbonates, alkyl carbamates) to give a biscarbamate, which typically passes through an intermediate purification stage and is then cleaved thermally in the second process step to diisocyanate and alcohol (EP 126 299, EP 126 300, EP 355 443, U.S. Pat. No. 4,713,476, U.S. Pat. No. 5,386,053). Alternatively, the actual biscarbamate formation may also be preceded by the separate preparation of a bisurea by controlled reaction of the diamine with urea (EP 568 782). Also conceivable is a two-stage sequence consisting of partial reaction of urea with alcohol in the first step and subsequent metered addition and carbamatization of the diamine in the second step (EP 657 420).

The thermal cleavage of (cyclo)aliphatic biscarbamates can be effected in the gas phase or in the liquid phase, with or without solvent and with or without catalysts. For instance, EP 126 299 and EP 126 300 disclose processes for preparing, respectively, hexamethylene diisocyanate and isophorone diisocyanate by cleaving the corresponding biscarbamates in the gas phase in a tubular reactor in the presence of metallic random packings at 410° C. Apart from the fact that such high temperatures can be established only with complicated technology, the process is afflicted with the disadvantage that partial decomposition of the reaction products already takes place at this temperature, associated with deposits on the random packings and blockage of the tubular reactor, and so the process is not very suitable for industrial production owing to the short service life.

There has therefore been no lack of attempts, by chemical and process technology measures, to achieve yield improvements and restrict undesired by-product formation. For instance, a series of documents describes the use of catalysts which accelerate the cleavage reaction of the biscarbamates (DE 1 022 222, U.S. Pat. No. 3,919,279, DE 2 635 490). Indeed, in the presence of suitable catalysts—these are a variety of basic, acidic and organometallic compounds—it is entirely possible to enhance the isocyanate yield compared to the uncatalyzed variant. However, the formation of undesired by-products cannot be avoided even through the presence of a catalyst. The same applies to the additional use of inert solvents, as likewise recommended in U.S. Pat. No. 3,919,279 and DE 2 635 490, in order to ensure homogeneous distribution of the heat supplied and of the catalyst within the reaction medium. In principle, the use of solvents which boil under reflux, however, results in a reduction in the space-time yield of isocyanates and is, moreover, afflicted with the disadvantage of an additional high energy expenditure.

Examples cited in EP 54 817 for the thermally catalyzed cleavage of monocarbamates describe the partial discharge of the reaction mixture to remove the resinifying by-products which form in the course of the carbamate cleavage. This procedure serves to prevent deposits and blockages in reactors and workup units. There are no indications which point to a yield-increasing utilization of the partial discharge. EP 61 013 describes a similar approach to a solution, the thermolysis in this case being performed in the presence of solvents whose purpose apparently consists in a better absorption of the nonvolatile by-products. Here too, the partial discharge is not utilized in the manner of a yield optimization.

EP 355 443 discloses that a yield increase can be achieved when the high molecular weight utilizable and nonutilizable by-products formed during the cleavage of the biscarbamates in the cleavage reactor, to ensure a disruption-free and selective reaction, are discharged very substantially continuously from the reactor and then converted for the most part in the presence of alcohol and then recycled into the (cyclo)alkylene biscarbamate synthesis. The procedure described is associated with high energy expenditure, since nonutilizable by-products are removed from the discharge of the (cyclo)alkylene biscarbamate synthesis by distillation, it being necessary to evaporate the entire biscarbamate. In contrast to EP 355 443, the biscarbamate discharge in the process of EP 566 925 is divided into two substreams, of which only one is freed by distillation from its high-boiling, nonutilizable by-products, before the contaminated biscarbamate streams are fed to the deblocking reaction in the cleavage reactor. In addition, the continuous cleavage reactor discharge in EP 566 925 is recycled directly, i.e. without a recarbamatization step, into the (cyclo)alkylene biscarbamate synthesis.

The preparation of (cyclo)aliphatic biscarbamates in a one-pot reaction from diamine, urea and alcohol with simultaneous removal of ammonia is known from EP 18 568. The teaching of EP 18 568 has been developed further and is described in EP 126 299, EP 126 300, EP 355 443, EP 566 925. The disadvantage of the simultaneous reaction of diamine, urea and alcohol undertaken there is the selectivity which is reduced by unavoidable side reactions, as a result of by-products which are inevitably formed in relatively large amounts, which have to be removed before the thermal deblocking of the biscarbamates. EP 568 782 therefore recommends a continuous process for preparing (cyclo)aliphatic diisocyanates, which comprises essentially three main steps, of which the first describes the formation of (cyclo)alkylenebisureas, the second the formation of (cyclo)alkylene biscarbamates from the (cyclo)alkylenebisureas, and the third the cleavage of the (cyclo)alkylene biscarbamates in the liquid phase to the desired (cyclo)aliphatic diisocyanates—i.e. the (cyclo)alkylene biscarbamate is prepared in two separate stages. According to the teaching of EP 568 782, the discharge of the reaction sequence composed of (cyclo)alkylenebisurea formation and subsequent (cyclo)alkylene biscarbamate synthesis is first freed by distillation from low and medium boilers such as alcohols, carbamates and carbonates, and the high boilers in the biscarbamate are removed thereafter by short-path evaporation. The (cyclo)alkylene biscarbamate is deblocked thermally and a portion of the cleavage bottoms is discharged continuously, recarbamatized with alcohol and recycled back into the (cyclo)alkylene biscarbamate synthesis stage.

It is also stated, in EP 1 634 868, that when (cyclo)aliphatic diamines are used, in addition to the one-stage synthesis of (cyclo)aliphatic biscarbamates from (cyclo)aliphatic diamines, alcohol and urea, it is advantageous to prepare the (cyclo)aliphatic biscarbamates by two-stage reaction, which thus proceeds via (cyclo)aliphatic bisurea, of (cyclo)aliphatic diamines with alcohol and urea, to free them of low and medium boilers, to thermally cleave the (cyclo)aliphatic biscarbamates thus purified to release the desired (cyclo)aliphatic diisocyanate, to continuously discharge a portion of the cleavage bottoms from the cleavage apparatus and to recarbamatize it with alcohol, to remove high boiler components therefrom and to recycle the recarbamatized material thus purified into the process, or else to directly remove the high boiler components from the portion of the cleavage bottoms discharged continuously from the cleavage apparatus, to recarbamatize the distillate obtained with alcohol and to recycle the recarbamatized material into the process. It has been found that these process steps firstly achieve a comparatively low steady-state concentration of high boiler components over the entire sequence of biscarbamate synthesis, biscarbamate purification and biscarbamate cleavage, such that deposits which are promoted especially by the high boiler components which are high in viscosity by nature can substantially be prevented, and good plant availability and a good process yield are also ensured over the long term. Secondly, the sequence of recarbamatization and high boiler removal, or high boiler removal with subsequent recarbamatization of the distillate, which follows downstream of the thermal cleavage reaction, has the advantage that, compared to the customary procedure in which the high boilers are removed before the biscarbamate cleavage, the amount of biscarbamate to be converted to the vapor phase is reduced significantly, which allows capital and energy costs to be saved.

In addition, EP 1 582 680 states that, when (cyclo)aliphatic diamines are used, it is advantageous to free the (cyclo)aliphatic biscarbamates of low and medium boilers after they have been synthesized by reacting (cyclo)aliphatic diamines with alcohol and urea and/or urea derivatives, to thermally cleave the (cyclo)aliphatic biscarbamates thus purified to release the desired (cyclo)aliphatic diisocyanate, to continuously discharge a portion of the cleavage bottoms from the cleavage apparatus and to remove high boiler components therefrom, and to recarbamatize the discharge thus purified with alcohol and to recycle it into the process. It has been found that it is possible in this way firstly to achieve a comparatively low steady-state concentration of high boiler components over the overall sequence of biscarbamate synthesis, biscarbamate purification and biscarbamate cleavage, such that deposits which are promoted especially by the high boiler components which are high in viscosity by nature can substantially be prevented, and good plant availability and a good process yield are also ensured over the long term. Secondly, the high boiler removal which follows downstream of the thermal cleavage reaction has the advantage that, compared to the customary procedure in which the high boilers are removed before the biscarbamate cleavage, the amount of biscarbamate to be converted to the vapor phase is reduced significantly, which allows capital and energy costs to be saved.

The currently predominant commercial form of urea prepared on the industrial scale is that of prills, i.e. small pellets with a diameter of 1-3 mm. Even at very low water contents of <0.1%, crystalline urea has such a strong tendency to cake that it is not an option for loose storage in large amounts. Improvement of the storage properties of urea prills, which appears to be necessary, for example, in the case of silo storage of large amounts, is achieved by a subsequent surface treatment of the prills with powders, for example talc, bentonites, kieselguhr, diatoms or other silicatic substances, or by sulfur and also by spray application of small amounts of oil.

The urea industry nowadays preferentially adds formaldehyde at up to 0.6% by weight (Ullmann's Encyclopedia of Industrial Chemistry, Release 2006, 7th Edition) to the urea melt before the prilling in order to increase the stability of the prills. This measure serves to prevent decomposition and caking in the course of transport, and to improve the storage stability.

Urea from a urea melt treated with formaldehyde (including paraformaldehyde) before the prilling or granulation, and urea surface treated with formaldehyde (including paraformaldehyde), likewise an industrially practiced measure for improving the storage properties of the prills, leads to the formation of undesired by-products both in the case of one-stage and two-stage processes and also alternatively after multistage processes for preparing (cyclo)aliphatic biscarbamates, and in the subsequent thermal cleavage of the (cyclo)aliphatic biscarbamates to (cyclo)aliphatic diisocyanates.

The by-products formed in the continuous one-stage or multistage biscarbamate synthesis, after a short run time, not only lead to undesired caking in the apparatus with the consequence of relatively short production periods with subsequent complex cleaning procedures, but are also removable only insufficiently in the known stages, and in the different stages described in detail in the literature, for distillative workup of the crude biscarbamate.

In the units for thermal cleavage of the (cyclo)aliphatic biscarbamate to the (cyclo)aliphatic diisocyanate, both the by-products which have not been removed quantitatively from the biscarbamate stage itself and a by-product spectrum newly generated therefrom lead additionally to caking and hence to reduction of the plant availability as a result of complex cleaning procedures.

It is an object of the invention to provide an improved process for preparing (cyclo)aliphatic diisocyanates, which avoids the abovementioned disadvantages.

The object is achieved, surprisingly, by using, for the continuous preparation of (cyclo)aliphatic diisocyanates by reacting (cyclo)aliphatic diamines with urea and/or urea equivalents (e.g. alkyl carbonates, alkyl carbamates) and alcohols to give (cyclo)aliphatic biscarbamates and subsequent thermal cleavage of the (cyclo)aliphatic biscarbamates to (cyclo)aliphatic diisocyanates to form the (cyclo)aliphatic biscarbamates by one-stage, two-stage and also alternatively by multistage processes, unconditioned urea, irrespective of the administration form (prills, granule, crystals, melt, solution). Unconditioned urea has neither been surface treated nor have additives and/or formaldehyde been added to the melt before the prilling or granulation.

The urea used in accordance with the invention and also the urea employed to prepare urea equivalents (e.g. alkyl carbonates, alkyl carbamates) as a possible precursor to the synthesis of the (cyclo)aliphatic biscarbamates is unconditioned, i.e. it must not have been surface treated with inorganic substances, for example with talc, bentonites, kieselguhr, diatoms, kaolin or other silicatic substances which find use as anticaking agents, and/or originate from a urea melt treated with formaldehyde (including paraformaldehyde) and/or be surface treated with formaldehyde (or paraformaldehyde). In general, the maximum formaldehyde concentration (including paraformaldehyde) of the urea used or of the urea equivalents used is 0.01 to 0.10% by weight, preferably 0.001 to 0.01% by weight and more preferably less than 0.001% by weight.

The process according to the invention has the advantage that a quantitative removal of the by-product spectrum typically generated with the distillation and rectification units described to purify the (cyclo)aliphatic diisocyanates can be omitted, and leads to diisocyanate qualities whose profile of performance properties enables use in further finishing stages without additional workup steps.

The removal of the by-product spectrum generated in the biscarbamate stage from formaldehyde and/or from formaldehyde-containing components of the unconditioned urea used in the reaction with (cyclo)aliphatic diamines in the presence of alcohols is not required, and the use of additional apparatus is unnecessary. Owing to the avoidance of by-products in the biscarbamate stage, in addition, a further by-product spectrum in the thermal cleavage of the (cyclo) aliphatic biscarbamates to (cyclo)aliphatic diisocyanates is subsequently avoided. In this stage of distillative purification of the diisocyanates too, the use of additional apparatus to achieve the desired diisocyanate purities is superfluous.

An additional capital investment associated with a significant reduction in the overall process yield resulting from diamine losses caused by by-product formation, which additionally reduce the plant availability owing to the caking caused in various apparatus parts as a result of complex cleaning procedures, has surprisingly been completely avoided by the inventive use of unconditioned ureas, thus enhancing the economic viability of the process.

The invention provides a process for continuously preparing (cyclo)aliphatic diisocyanates by reacting at least one (cyclo)aliphatic diamine with urea and/or urea equivalents and at least one alcohol to give (cyclo)aliphatic biscarbamates and subsequently thermally cleaving the (cyclo)aliphatic biscarbamates to (cyclo)aliphatic diisocyanates, characterized in that the (cyclo)aliphatic biscarbamates are formed by using unconditioned urea and/or urea equivalents prepared from unconditioned urea.

The invention preferably provides a multistage process for continuously preparing (cyclo)aliphatic diisocyanates by reacting at least one (cyclo)aliphatic diamine with urea and/or urea equivalents, for example alkyl carbonates, alkyl carbamates, and at least one alcohol to give (cyclo)aliphatic biscarbamates and subsequently thermally cleaving the (cyclo)aliphatic biscarbamates to (cyclo)aliphatic diisocyanates, characterized in that the (cyclo)aliphatic biscarbamates are formed by one-stage, two-stage or else alternatively multistage processes by using, irrespective of the administration form (e.g. prills, granule, crystals, melt, solution), unconditioned urea and/or urea equivalents prepared from unconditioned urea (also referred to as carbonic acid derivatives, for example alkyl carbonates, alkyl carbamates).

The maximum formaldehyde concentration (including paraformaldehyde) of the urea used or of the urea equivalents used is 0.01 to 0.10% by weight, preferably 0.001 to 0.01% by weight and more preferably less than 0.001% by weight.

The invention provides a process for continuously preparing (cyclo)aliphatic diisocyanates of the formula (I)

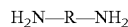

OCN—R—NCO where R is a straight-chain or branched aliphatic hydrocarbon radical having a total of 6 to 12 carbon atoms or an optionally substituted cycloaliphatic hydrocarbon radical having a total of 4 to 18 and preferably 5 to 15 carbon atoms, by reacting (cyclo)aliphatic diamines with unconditioned urea and/or urea equivalents prepared from unconditioned urea and alcohols to give (cyclo)aliphatic biscarbamates and the thermal cleavage thereof, which is characterized by the following individual steps:

a) (cyclo)aliphatic diamines of the formula (II)

H₂N—R—NH₂ where R is a straight-chain or branched aliphatic hydrocarbon radical having a total of 6 to 12 carbon atoms or an optionally substituted cycloaliphatic hydrocarbon radical having a total of 4 to 18 and preferably 5 to 15 carbon atoms are reacted with unconditioned urea and/or urea equivalents prepared from unconditioned urea in the presence of alcohol of the formula (III)

R¹—OH where R¹ is a radical as remains after removal of the hydroxyl group from a primary or secondary (cyclo) aliphatic alcohol having 3 to 8 carbon atoms, in the absence or presence of dialkyl carbonates, alkyl carbamates or mixtures of dialkyl carbonates and carbamic esters, and in the absence or presence of catalysts, to give (cyclo)alkylenebisurea of the formula (IV)

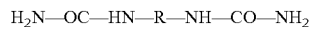

H₂N—OC—HN—R—NH—CO—NH₂ where R is a straight-chain or branched aliphatic hydrocarbon radical having a total of 6 to 12 carbon atoms or an optionally substituted cycloaliphatic hydrocarbon radical having a total of 4 to 18 and preferably 5 to 15 carbon atoms, in a distillation reactor, with simultaneous removal of the ammonia formed, the reactants being introduced continuously to the uppermost tray and the ammonia formed being driven out by distillation with alcohol vapors which are introduced in the bottom;

b) in the second stage, the reaction of the (cyclo)alkylenebisurea obtained from the first stage a) with the alcohol used as solvent in a) is performed in a pressure distillation reactor with simultaneous removal of the ammonia formed to give the (cyclo)alkylene biscarbamate of the formula (V)

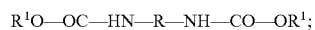

R¹O—OC—HN—R—NH—CO—OR¹;

c) or optionally the reaction of (cyclo)aliphatic diamines of the formula (II)

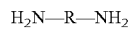

H₂N—R—NH₂ with unconditioned urea and/or urea equivalents prepared from unconditioned urea, in the presence of alcohol of the formula (III)

R¹—OH, is performed in a pressure distillation reactor in one stage with simultaneous removal of the ammonia formed to give the (cyclo)alkylene biscarbamate of the formula (V)

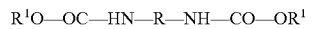

R¹O—OC—HN—R—NH—CO—OR¹ without steps a) and b) (R and R¹ correspond to the above definition);

d) the alcohol, the dialkyl carbonates and/or alkyl carbamates are removed from the reaction mixture obtained from b) or optionally c), and the alcohol and optionally also the dialkyl carbonates and/or alkyl carbamates are recycled into reaction stage a) or b) or optionally c);

e) the removal of ammonia from the vapors obtained at the top of the pressure distillation reactor either from b) or optionally from c), and from the alcohol which is obtained by partial condensation of the vapors from the distillation reactor a) or optionally c), is performed in a downstream column, appropriately under the pressure of the pressure distillation reactor, the ammonia-free alcohol obtained in the bottom being recycled into the bottom of the distillation reactor and/or into the bottom of the pressure distillation reactor;

f) the crude (cyclo)alkylene biscarbamate depleted of low boilers from d) is removed completely or partially from high-boiling residues, or a residue removal is optionally omitted;

g) the reaction mixture which contains (cyclo)alkylene biscarbamates and has been pretreated by means of steps d) and optionally f) is cleaved thermally in the presence of a catalyst, continuously and without solvent, at temperatures of 180 to 280° C., preferably 200 to 260° C., and under a pressure of 0.1 to 200 mbar, preferably 0.2 to 100 mbar, in such a way that a portion of the reaction mixture of 10 to 60% by weight based on the feed, preferably 15 to 45% by weight based on the feed, is discharged continuously from the bottom;

h) the cleavage products from step g) are separated by rectification into a (cyclo)aliphatic crude diisocyanate and alcohol;

i) the (cyclo)aliphatic crude diisocyanate is purified by distillation and the fraction containing (cyclo)aliphatic pure diisocyanate is isolated;

j) the bottoms discharge from g) is reacted partially or completely with the alcohol from h) in the presence or absence of catalysts within 1 to 150 min, preferably 3 to 60 min, at temperatures of 20 to 200° C., preferably 50 to 170° C., and at a pressure of 0.5 to 20 bar, preferably 1 to 15 bar, where the molar ratio of NCO groups and OH groups is up to 1:100, preferably 1:20 and more preferably 1:10;

k) the reaction mixture from j) is separated into a material of value stream and a waste stream, and the waste stream which is rich in high boiler components is discharged from the process and discarded;

l) optionally the reaction mixture from j) is recycled directly into the (cyclo)alkylene biscarbamate stage b) or optionally c);

m) a portion of the bottoms fraction of the purifying distillation i) is discharged continuously and conducted into the cleavage reaction g) and/or into the carbamatization stage j);

n) optionally the top fractions obtained in the purifying distillation of the (cyclo)aliphatic crude diisocyanate are likewise recycled into the carbamatization stage j);

o) the material of value stream from k) is recycled into stage b) or optionally c) and/or d) and/or g).

The invention also provides a multistage process for continuously preparing (cyclo)aliphatic diisocyanates of the formula (I)

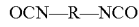

where R is a straight-chain or branched aliphatic hydrocarbon radical having a total of 6 to 12 carbon atoms or an optionally substituted cycloaliphatic hydrocarbon radical having a total of 4 to 18 and preferably 5 to 15 carbon atoms, by reacting (cyclo)aliphatic diamines with unconditioned urea and/or urea equivalents prepared from unconditioned urea and alcohols to give (cyclo)aliphatic biscarbamates and the thermal cleavage thereof, wherein a) (cyclo)aliphatic diamines of the formula (II)

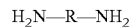

where R is a straight-chain or branched aliphatic hydrocarbon radical having a total of 6 to 12 carbon atoms or an optionally substituted cycloaliphatic hydrocarbon radical having a total of 4 to 18 and preferably 5 to 15 carbon atoms are reacted with unconditioned urea and/or urea equivalents prepared from unconditioned urea in the presence of alcohol of the formula (III)

where $R^1$ is a radical as remains after removal of the hydroxyl group from a primary or secondary (cyclo)aliphatic alcohol having 3 to 8 carbon atoms, in the absence or presence of dialkyl carbonates, alkyl carbamates or mixtures of dialkyl carbonates and carbamic esters, and in the absence or presence of catalysts, to give (cyclo)alkylenebisurea of the formula (IV)

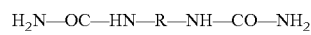

where R is a straight-chain or branched aliphatic hydrocarbon radical having a total of 6 to 12 carbon atoms or an optionally substituted cycloaliphatic hydrocarbon radical having a total of 4 to 18 and preferably 5 to 15 carbon atoms, in a distillation reactor, with simultaneous removal of the ammonia formed, the reactants being introduced continuously to the uppermost tray and the ammonia formed being driven out by distillation with alcohol vapors which are introduced in the bottom;

b) in the second stage, the reaction of the (cyclo)alkylenebisurea obtained from the first stage a) with the alcohol used as solvent in a) is performed in a pressure distillation reactor with simultaneous removal of the ammonia formed to give the (cyclo)alkylene biscarbamate of the formula (V)

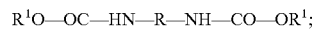

c) or optionally the reaction of (cyclo)aliphatic diamines of the formula (II)

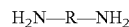

with unconditioned urea and/or urea equivalents prepared from unconditioned urea, in the presence of alcohol of the formula (III)

is performed in a pressure distillation reactor in one stage with simultaneous removal of the ammonia formed to give the (cyclo)alkylene biscarbamate of the formula (V)

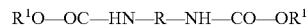

without steps a) and b) (R and $R^1$ correspond to the above definition);

d) the alcohol, the dialkyl carbonates and/or alkyl carbamates are removed from the reaction mixture obtained from b) or optionally c), and the alcohol and optionally also the dialkyl carbonates and/or alkyl carbamates are recycled into reaction stage a) or b) or optionally c);

e) the removal of ammonia from the vapors obtained at the top of the pressure distillation reactor either from b) or optionally from c), and from the alcohol which is obtained by partial condensation of the vapors from the distillation reactor a) or optionally c), is performed in a downstream column, appropriately under the pressure of the pressure distillation reactor, the ammonia-free alcohol obtained in the bottom being recycled into the bottom of the distillation reactor and/or into the bottom of the pressure distillation reactor;

f) the crude (cyclo)alkylene biscarbamate depleted of low boilers from d) is removed completely or partially from high-boiling residues, or a residue removal is optionally omitted;

g) the reaction mixture which contains (cyclo)alkylene biscarbamates and has been pretreated by means of steps d) and optionally f) is cleaved thermally in the presence of a catalyst, continuously and without solvent, at temperatures of 180 to 280° C., preferably 200 to 260° C., and under a pressure of 0.1 to 200 mbar, preferably 0.2 to 100 mbar, in such a way that a portion of the reaction mixture of 10 to 60% by weight based on the feed, preferably 15 to 45% by weight based on the feed, is discharged continuously from the bottom;

h) the cleavage products from step g) are separated by rectification into a (cyclo)aliphatic crude diisocyanate and alcohol;

i) the (cyclo)aliphatic crude diisocyanate is purified by distillation and the fraction containing (cyclo)aliphatic pure diisocyanate is isolated;

j) the bottoms discharge from g) is reacted partially or completely with the alcohol from h) in the presence or absence of catalysts within 1 to 150 min, preferably 3 to 60 min, at temperatures of 20 to 200° C., preferably 50 to 170° C., and at a pressure of 0.5 to 20 bar, preferably 1 to 15 bar, where the molar ratio of NCO groups and OH groups is up to 1:100, preferably 1:20 and more preferably 1:10;

k) the reaction mixture from j) is separated into a material of value stream and a waste stream, and the waste stream which is rich in high boiler components is discharged from the process and discarded;

l) optionally the reaction mixture from j) is recycled directly into the (cyclo)alkylene biscarbamate stage b) or optionally c);

m) a portion of the bottoms fraction of the purifying distillation i) is discharged continuously and conducted into the cleavage reaction g) and/or into the carbamatization stage j);

n) optionally the top fractions obtained in the purifying distillation of the (cyclo)aliphatic crude diisocyanate are likewise recycled into the carbamatization stage j);

o) the material of value stream from k) is recycled into stage b) or optionally c) and/or d) and/or g).

By the process according to the invention, it is possible to prepare (cyclo)aliphatic diisocyanates, i.e. aliphatic and cycloaliphatic, with very good yield and high purities without any problem in continuous operation. What is advantageous in the multistage process according to the invention is especially the fact that, when unconditioned urea and/or urea equivalents prepared from unconditioned urea, also referred to as carbonic acid derivatives, for example alkyl carbonates, alkyl carbamates, with simultaneous use of (cyclo)aliphatic diamines of the formula (II), are used as starting materials for continuous diisocyanate synthesis, caking and deposits which are caused by conditioned urea and are promoted especially by the negative properties of the high-viscosity high boiler components can substantially be prevented. Moreover, the use of unconditioned urea is considered to be advantageous since material wear and erosion up to and including destruction of moving apparatus parts, which occurs as a result of the eroding properties of conditioned urea, for example comprising inorganic anticaking agents, can be avoided, thus also ensuring good plant availability over the long term. Moreover, it is a significant advantage that, in contrast to urea conditioned principally with formaldehyde or formaldehyde-containing components, which causes undesired by-products which are removable only with very great difficulty in the different process stages, the use of unconditioned urea and/or urea equivalents prepared from unconditioned urea allows diisocyanate qualities with high purities to be prepared, whose profile of performance properties does not cause any doubt as to use in further value addition stages.

In the text which follows, the terms diamine, alcohol, bisurea, biscarbamate and diisocyanate are used in the sense of the abovementioned definitions.

a) The reaction of diamine with unconditioned urea and/or urea equivalents prepared from unconditioned urea, also referred to as carbonic acid derivatives, for example alkyl carbonates, alkyl carbamates, where the maximum formaldehyde concentration (including paraformaldehyde) of the urea used or of the urea equivalents used must be 0.01 to 0.10% by weight, preferably 0.001 to 0.01% by weight and more preferably <0.001% by weight, to give the bisurea in the presence of alcohol as a solvent is effected in a distillation reactor. The reactants are introduced continuously to the uppermost tray of the distillation reactor, and the ammonia released is driven out by alcohol vapors which are introduced in the bottom of the distillation reactor. The ammonia/alcohol mixture is, in order to prevent the deposition of ammonium carbamate, partially condensed in a condenser at temperatures of 30 to 50° C. Ammonia-free alcohol is recovered from the condensate by distillation in the column connected downstream of the pressure distillation reactor.

The molar ratio of the diamine:urea:alcohol reactants is 1:2.0 to 2.4:3 to 10. The distillation reactor has at least four trays. The reaction is performed at temperatures of 100 to 130° C. and pressures of 0.7 to 1.5 bar (abs.). The residence time required in the distillation reactor is 4 to 10 h, preferably 6 to 8 h. The amount of alcohol introduced in the bottom to drive out the ammonia is 0.05 to 3 kg/kg and preferably 0.1 to 1 kg/kg of bisurea, the amount of alcohol thus introduced being drawn off together with the ammonia formed at the top, being partially condensed and then freed of residual ammonia in an alcohol recovery column, and being recycled into the bottom.

In order to achieve very substantially complete conversion of the urea to the bisurea, the reaction temperature is limited to a maximum of 130° C. The reaction rate which arises from the desired reaction temperature, and the type and the ratio of the reactants, determines the residence time and hence the dimensions of the distillation reactor.

b) The crude bisurea dissolved in alcohol, which is obtained in the bottom of the distillation reactor, is conducted continuously into a second reactor in which the conversion to the biscarbamate is effected at elevated temperature and elevated pressure, which again releases ammonia which has to be removed from the reaction mixture for reasons of chemical equilibrium. The further conversion of the crude bisurea from a) is effected preferably in a pressure distillation reactor and at a molar ratio of bisurea to alcohol of 1:5 to 12. The stream from a) is preferably conducted continuously to the uppermost tray of the pressure distillation reactor, with optional supply of the reaction mixture from j). The reaction takes place in the absence or presence of catalysts at reaction temperatures of 140 to 270° C., preferably 160 to 250° C., and under a pressure which is 5 to 20 bar, preferably 7 to 15 bar, within 2 to 20 hours, preferably 8 to 15 hours. The continuous driving-out of the ammonia released is promoted by alcohol vapors which are introduced into the bottom of the pressure distillation reactor in an amount of 0.5 to 8 kg/kg and preferably 1 to 4 kg/kg of biscarbamate formed, and appropriately generated in an evaporator mounted at the bottom of the column.

c) This procedure is effected without steps a) and b) in a one-stage process step. To prepare the biscarbamates in reaction stage c), the diamines of the formula (II) are reacted with unconditioned urea and/or urea equivalents prepared from unconditioned urea, also referred to as carbonic acid derivatives, for example alkyl carbonates, alkyl carbamates, and an alcohol of the formula (III), optionally including mixtures of such alcohols, in a molar ratio of 1:2.01:4.0 to 1:2.2:10, preferably 1:2.02:6 to 1:2.12:9, where the second numerical value specified in the molar ratio is based on moles of urea, optionally but not preferably in the presence of dialkyl carbonates, alkyl carbamates or mixtures of dialkyl carbonates and carbamic esters, in an amount of in each case 1-10 mol % based on the diamine, with optional supply of the reaction mixture from j), in the absence or presence of catalysts, at reaction temperatures of 140-270° C., preferably 160-250° C., and under a pressure which, depending on the alcohol used, is between 2-80 bar, preferably 7-15 bar, within 2 to 20 hours, preferably 4-9 hours. The reaction can be effected in a continuous stirred tank cascade, but preferably in a pressure distillation reactor.

To increase the reaction rate, the biscarbamates can be prepared in the presence of catalysts. Suitable catalysts are inorganic or organic compounds which contain one or more cations, preferably one cation, of metals of groups IA, IB, IIA, IIB, IIIA, IIIB, IVA, IVB, VA, VB, VIB, VIIB and VIIIB of the Periodic Table, defined according to the Handbook of Chemistry and Physics 14th Edition, published by Chemical Rubber Publishing Co. 2310 Superior Ave. N.E. Cleveland, Ohio, for example halides such as chlorides and bromides, sulfates, phosphates, nitrates, borates, alkoxides, phenoxides, sulfonates, oxides, oxide hydrates, hydroxides, carboxylates, chelates, carbonates and thio- or dithiocarbamates. Examples include the cations of the following metals: lithium, sodium, potassium, magnesium, calcium, aluminum, gallium, tin, lead, bismuth, antimony, copper, silver, gold, zinc, mercury, cerium, titanium, vanadium, chromium, molybdenum, manganese, iron, cobalt and nickel. Examples of typical catalysts include the following compounds: lithium ethoxide, lithium butoxide, sodium methoxide, potassium tert-butoxide, magnesium ethoxide, calcium methoxide, tin(II) chloride, tin(IV) chloride, lead acetate, aluminum trichloride, bismuth trichloride, copper(II) acetate, copper(II) chloride, zinc chloride, zinc octoate, titanium tetrabutoxide, vanadium trichloride, vanadium acetylacetonate, manganese(II) acetate, iron(II) acetate, iron(III) acetate, iron oxalate, cobalt chloride, cobalt naphthenate, nickel chloride, nickel naphthenate and mixtures thereof. The catalysts may optionally be used in the form of their hydrates or ammoniates.

The starting compounds for the process according to the invention are diamines of the formula (II) already specified above, alcohols of the formula (III) already specified above and unconditioned urea and/or urea equivalents prepared from unconditioned urea.

Suitable diamines of the formula (II) are aliphatic diamines, for example hexamethylenediamine, 2-methylpentamethylenediamine, octamethylenediamine, 2,2,4- and 2,4,4-trimethylhexamethylenediamine or mixtures thereof, decamethylenediamine, 2-methylnonamethylenediamine, dodecamethylenediamine, and cycloaliphatic diamines, for example 1,4-cyclohexanediamine, 1,3- or 1,4-cyclohexanedimethanamine, 5-amino-1,3,3-trimethylcyclohexanemethanamine (isophoronediamine), 4,4'methylenedicyclohexyldiamine, 2,4-methylenedicyclohexyldiamine, 2,2'-methylenedicyclohexyldiamine and isomeric (cyclo)aliphatic diamines, and also perhydrogenated methylenediphenyldiamine.

As a result of the preparation, methylenediphenyldiamine (MDA) is obtained as an isomer mixture of 4,4'-, 2,4- and 2,2'-MDA (see, for example, DE 101 27 273). Perhydrogenated methylenediphenyldiamine is obtained by full hydrogenation from MDA and is accordingly a mixture of isomeric methylenedicyclohexyldiamines ($H_{12}MDA$), specifically 4,4'-, 2,4- and 2,2'-$H_{12}$MDA, and possibly small amounts of incompletely converted (partly) aromatic MDA. Preference is given to using, as diamines of the formula (II), 5-amino-1,3,3-trimethylcyclohexanemethanamine (isophoronediamine), 2,2,4- and 2,4,4-trimethylhexamethylenediamine or mixtures thereof, 4,4'-methylenedicyclohexyldiamine, 2,4-methylenedicyclohexyldiamine and 2,2'-methylenedicyclohexyldiamine, and also any desired mixtures of at least two of these isomers, and also hexamethylenediamine and/or 2-methylpentamethylenediamine.

Suitable alcohols of the formula (III) are any desired aliphatic or cycloaliphatic alcohols which have a boiling point below 190° C. under standard pressure. Examples include C1-C6-alkanols, for example methanol, ethanol, 1-propanol, 1-butanol, 2-butanol, 1-hexanol or cyclohexanol. Preference is given to using 1-butanol as the alcohol.

In the course of conversion of the reaction mixture, ammonia is released, the removal of which from the reaction equilibrium has been found to be advantageous. When the ammonia is discharged from the reactor, it should be ensured that the wall temperatures of the reactor and of the discharge tube are above 60° C., in order that coverage by ammonium carbamate, which is formed in minimal amounts from ammonia and carbon dioxide as a result of decomposition of urea, can be prevented. It has been found to be useful, for example, to perform the reaction in a pressure distillation reactor, in which case the reaction mixture is conducted in countercurrent to alcohol vapors introduced in the bottom, and in this way such intense mixing of the liquid is effected on the trays, which correspond virtually in each case to a cascade stage.

d) The excess alcohol, the dialkyl carbonates if any have been formed, or alkyl carbamates, or mixtures of at least two of these components, are removed in one stage, or advantageously in two stages. At the first stage, the reaction mixture is decompressed from the pressure level of reaction stage b) or optionally c) to a pressure of 1 to 500 mbar, preferably 2 to 150 mbar, and in this way separated into gaseous vapors which contain the predominant amount of alcohol, with or without dialkyl carbonates and/or alkyl carbamates, and into a liquid discharge. In the second step, the liquid discharge is freed by thin film evaporation at 180 to 250° C., preferably 200 to 230° C., and a pressure of 0.1 to 20 mbar, preferably 1 to 10 mbar, of any residual butanol present, and also medium boilers such as dialkyl carbonates and/or alkyl carbamates, such that the residue consists essentially of the monomeric biscarbamate and any high-boiling oligomers. After further distillative purification, the vapors can be recycled into reaction stage a), b) or optionally c). Recycling of the dialkyl carbonates and/or alkyl carbamates into reaction stage b) or optionally c) is possible but not required.

e) The vaporous mixture of alcohol and ammonia drawn off at the top of the pressure distillation reactor from b) or optionally c) is, without condensing it, preferably conducted under the pressure of the pressure distillation reactor into the middle region of a distillation column in which rectification in the bottom at at least 170° C., according to the alcohol selected and operating pressure, affords ammonia-free alcohol which is recycled into the bottom of the distillation reactor a) and of the pressure distillation reactor b), or optionally c). The ammonia is drawn off in liquid form at the top. In order to prevent the coverage of the reflux condenser by any ammonium carbamate present, an appropriate proportion of alcohol is permitted for the temperature increase at the top to at least 60° C. The amount of alcohol thus discharged from the circuit with the ammonia must be replaced by fresh alcohol.

f) Preferably, the liquid stream from step b) or optionally c), which contains monomeric biscarbamates with or without high-boiling oligomers and is obtained after removal of low and medium boilers is separated, preferably with the aid of a thin film or short path evaporator, at a temperature of 180 to 270° C., preferably 200 to 250° C., and under a pressure of 0.01 to 10 mbar, preferably 0.02 to 5 mbar, by distillation into a material of value stream which contains the monomeric biscarbamates and the lower-boiling by-products, and an undistillable by-product stream. The undistillable by-product stream which contains the high-boiling components is discharged from the preparation process and is typically discarded as a residue which cannot be utilized as a material.

Optionally, the stream which may contain high-boiling oligomers from stage b) or optionally c), before the above-described distillative purification thereof, can also be divided into two substreams, one of which is fed directly to the deblocking reaction (see g)) and the other first passes through the high boiler removal just described.

Optionally, it is possible to dispense with the removal of the high boilers which may be present in the reaction mixture from stage d), when the separation, described under k), of the recarbamatized stream from stage j) is performed.

g) The material of value stream from stage d) and optionally from stage f), containing the monomeric biscarbamates and the lower-boiling by-products, is continuously thermally cleaved in a suitable apparatus, partially and without solvent in the liquid phase in the presence of catalysts at temperatures of 180 to 280° C., preferably 200 to 260° C., and under a pressure of 0.1 to 200 mbar, preferably 0.2 to 100 mbar. The conversion of biscarbamate to diisocyanate in the apparatus for thermal cleavage can be selected freely depending on the biscarbamate used, and is typically within a range from 10 to 95% by weight, preferably 35 to 85% by weight, of the amount of biscarbamate supplied (feed). The uncleaved proportion of the reaction mixture, which contains unconverted biscarbamates, high-boiling by-products and other reutilizable and unutilizable by-products, is discharged continuously. The amount of the discharge is guided by factors including the desired conversion and the desired capacity of the cleavage reaction, and can readily be determined experimentally. It is typically 10 to 60% by weight, preferably 15 to 45% by weight, based on the feed.

The catalysts used for the chemical cleavage of the biscarbamates include, for example, the aforementioned inorganic and organic compounds which catalyze the carbamate formation. Preference is given to using chlorides of zinc, tin or copper, and also zinc oxides, manganese oxides, iron oxides or cobalt oxides, the catalyst being metered into the mass flow from stage f) or optionally c) or optionally d) before it is fed into the cleavage as a 0.01 to 25% by weight, preferably 0.05 to 10% by weight, solution or suspension in the alcohol which is also used for carbamate preparation, in an amount of 5 to 400 ppm, preferably 10 to 100 ppm.

Suitable cleavage apparatus includes, for example, cylindrical cleavage reactors, for example tube ovens, or preferably evaporators, for example falling-film, thin-film or bulk evaporators, for example Robert evaporators, Herbert evaporators, caddle-type evaporators, Oskar evaporators and heating cartridge evaporators.

Preference is given to performing the cleavage in a combined cleavage and rectification column which is equipped, for the energy supply, with a falling-film evaporator in the bottom, with a device for additional energy input or for energy recovery in the lower third, with a device for removal of preferably crude diisocyanate in the upper third, and with a condenser, condensate collecting vessel and a pump for the reflux and the removal of pure alcohol at the top.

Owing to the reactivity of the isocyanate groups, the mean residence time thereof in the cleavage zone should be at a minimum, which is achieved by minimizing the liquid volume through appropriate construction measures and through use of structured packings with low 'holdup', and through very substantially immediate distillative removal of the diisocyanate formed from the cleavage zone. The latter is achieved by appropriate energy input in the bottom of the combined cleavage and rectification column. This establishes a concentration profile in the column, where essentially biscarbamate, less than 10% by weight and preferably less than 3% by weight of diisocyanate and undetectable amounts of alcohol are present in the bottom, while the liquid in the lower part of the column contains only small amounts of biscarbamate, but consists essentially of monoisocyanato-monocarbamate. The reflux required for this purpose is appropriately generated by a condensation stage above the cleavage zone and below the diisocyanate side draw. This mode of operation is particularly economically viable, since the energy to be removed here is obtained at a relatively high temperature level and can subsequently be utilized once again, for example to heat other product streams. Moreover, this correspondingly reduces the amount of vapor, such that the diameter of the column can be reduced correspondingly above this partial condenser.

In spite of the very substantially immediate distillative removal of the diisocyanate formed from the cleavage zone, the formation of relatively high molecular weight compounds cannot be prevented completely, and so a corresponding proportion from the bottom of the combined cleavage and rectification column has to be discharged continuously and treated further j).

Summarized briefly, the principal concern in the stage of thermal cleavage of the biscarbamates is to minimize the mean residence time of the isocyanate groups, which are inevitably released when deblocking the alcohol, in the cleavage zone and thus to restrict undesired side reactions to a minimum.

h) The cleavage products formed in the thermal cleavage, which are composed in particular of alcohol, diisocyanate and partially cleaved biscarbamates, are separated by rectification at temperatures of 95 to 260° C., preferably 110 to 245° C., and a pressure of 0.5 to 250 mbar, preferably 1 to 100 mbar, into alcohol and into a crude diisocyanate mixture consisting of (cyclo)aliphatic diisocyanate, partially cleaved (cyclo)aliphatic biscarbamate, the monoisocyanatomonocarbamate, and possibly small fractions of (cyclo)aliphatic biscarbamate. This separation can be carried out, for example, in the abovementioned combined cleavage and rectification column.

i) The crude mixture which is preferably obtained by rectification and consists of (cyclo)aliphatic diisocyanate, partially cleaved (cyclo)aliphatic biscarbamate, the monoisocyanatomonocarbamate, and possibly small proportions of (cyclo)aliphatic biscarbamate is purified by distillation at a temperature of 95 to 260° C., preferably 110 to 245° C., and under a pressure of 0.5 to 150 mbar, preferably 1 to 75 mbar, the fractions obtained being recycled or isolated as a pure product.

j) The bottoms discharge from the deblocking stage g) is combined partially or completely with the alcohol from the rectification stage h), the molar ratio of NCO groups and OH groups being up to 1:100, preferably 1:20 and more preferably 1:10, and the reaction mixture is converted in the presence or absence of catalysts within 1 to 150 min, preferably 3 to 60 min, at temperatures of 20 to 200° C., preferably 50 to 170° C., and at a pressure of 0.5 to 20 bar, preferably 1 to 15 bar. The reaction can be performed in a continuous tank cascade or in a tubular reactor. Useful catalysts are in principle all catalysts which promote the NCO/OH reaction. Examples include tin octoate, dibutyltin laurate, tin dichloride, zinc dichloride, copper chloride, copper dichloride, iron dichloride, iron trichloride and triethylamine.

k) The reurethanized stream from stage j) is separated into a material of value stream and a waste stream, and the waste stream rich in high boiler components is discharged from the process and discarded. The two streams are separated preferably by distillation with the aid of a thin film evaporator or short path evaporator, at a temperature of 180 to 270° C., preferably 200 to 250° C., and under a pressure of 0.01 to 10 mbar, preferably 0.02 to 5 mbar. The material of value stream which contains the monomeric carbamates and the lower-boiling by-products is obtained as the distillate. The waste stream rich in high-boiling components is obtained as the residue and is discharged from the preparation process and is typically discarded as a material which is unutilizable as a substance. Alternatively, but not preferably, the separation into material of value and waste can also be effected by extraction. A suitable extractant is, for example, supercritical carbon dioxide.

Optionally, the reurethanized stream from stage j) can also be divided before the above-described distillative purification into two substreams, one of which is fed directly to the purification stage d). The two streams can be divided in a ratio of 99:1 to 1:99, preferably 99:5 to 5:95. Optionally, the reurethanized stream leading to the high boiler removal can first be freed partially or completely of excess alcohol. This is preferably done by distillation. The alcohol removed can, as desired, be recycled into stage a) and/or b) and/or c) and/or preferably stage d).

l) The reurethanized stream from stage j) can, before a distillative purification, also be fed directly into the (cyclo) alkylene biscarbamate stage b) or optionally also c).

m) A portion of the bottoms fraction of the purifying distillation i) is discharged continuously and optionally recycled into the deblocking stage g) or preferably into the carbamatization stage j). The amount of the discharge is 0.1 to 50% by weight, preferably 0.2 to 25% by weight, of the feed of crude diisocyanate into the purifying distillation stage.

n) The top fraction of the purifying distillation stage i) can be discarded or preferably recycled into the carbamatization stage j). The amount of the top fraction removed per unit time is 0.1 to 3% by weight, preferably 0.3 to 1% by weight, of the feed of crude diisocyanate into the purifying distillation.

o) The purified reurethanized stream from stage k) is recycled into the (cyclo)alkylene biscarbamate stage b) or optionally also c), and/or into the low boiler and medium boiler removal d) and/or into the carbamate cleavage g).

The multistage process according to the invention for continuously preparing (cyclo)aliphatic diisocyanates by reacting (cyclo)aliphatic diamines with unconditioned (untreated) urea and/or urea equivalents (e.g. alkyl carbonates, alkyl carbamates) prepared from unconditioned (untreated) urea and alcohols to give (cyclo)aliphatic biscarbamates and subsequent thermal cleavage of the (cyclo)aliphatic biscarbamates to (cyclo)aliphatic diisocyanates makes it possible to produce (cyclo)aliphatic diisocyanates with high purities in reactions which proceed selectively and without disruption. The process according to the invention is suitable especially for preparing aliphatic diisocyanates with a straight-chain or branched aliphatic hydrocarbon radical having a total of 6 to 12 carbon atoms, such as hexamethylene diisocyanate, 2-methylpentane diisocyanate, 2,2,4- and 2,4,4-trimethylhexamethylene diisocyanate or mixtures thereof, octamethylene diisocyanate, decamethylene diisocyanate, 2-methylnonamethylene diisocyanate, dodecamethylene diisocyanate, or an optionally substituted cycloaliphatic hydrocarbon radical having a total of 4 to 18 and preferably 5 to 15 carbon atoms, for example 1,4-diisocyanatocyclohexane, 1,3- or 1,4-cyclohexanedimethane isocyanate, 5-isocyanato-1,3,3-trimethylcyclohexanemethane isocyanate (isophorone diisocyanate), 4,4'-methylenedicyclohexyl diisocyanate (4,4'-$H_{12}$MDI), 2,2'-methylenedicyclohexyl diisocyanate (2,2'-$H_{12}$MDI), 2,4'-methylenedicyclohexyl diisocyanate (2,4'-$H_{12}$MDI), or else mixtures of the aforementioned isomeric methylenedicyclohexyl diisocyanates ($H_{12}$MDI). Very particular preference is given to preparing 5-isocyanato-1,3,3-trimethylcyclohexanemethane isocyanate (isophorone diisocyanate), 2,2,4- and 2,4,4-trimethylhexamethylene diisocyanate or mixtures thereof, and 4,4'-methylenedicyclohexyl diisocyanate, and also any desired mixtures of 4,4'-$H_{12}$MDI, 2,4-$H_{12}$MDI and 2,2'-$H_{12}$MDI.

The (cyclo)aliphatic diisocyanates prepared are very suitable for production of polymers containing urethane, isocyanurate, amide and/or urea groups by the polyisocyanate polyaddition process. They additionally find use for preparation of polyisocyanate mixtures modified with urethane, biuret and/or isocyanurate groups. Such polyisocyanate mixtures of (cyclo)aliphatic diisocyanates are used especially to prepare high-value light-stable polyurethane coatings.

The invention also provides formaldehyde-free (cyclo)aliphatic diisocyanates obtainable by processes for continuously preparing (cyclo)aliphatic diisocyanates by reacting at least one (cyclo)aliphatic diamine with urea and/or urea equivalents and at least one alcohol to give (cyclo)aliphatic biscarbamates and then thermally cleaving the (cyclo)aliphatic biscarbamates to (cyclo)aliphatic diisocyanates, characterized in that the (cyclo)aliphatic biscarbamates are formed by using unconditioned urea and/or urea equivalents prepared from unconditioned urea, especially formaldehyde-free (cyclo)aliphatic diisocyanates selected from isophorone diisocyanate, trimethylhexamethylene diisocyanate, $H_{12}MDI$ and hexamethylene diisocyanate (HDI).

"Formaldehyde-free" means that the maximum formaldehyde concentration (including paraformaldehyde) of the urea used or of the urea equivalents used is 0.01 to 0.10% by weight, preferably 0.001 to 0.01% by weight and more preferably less than 0.001% by weight.

The invention is illustrated in detail by the examples which follow.

Examples 1 to 4 describe the preparation of (cyclo)aliphatic diisocyanates using unconditioned urea with a formaldehyde content of <10 ppm. Comparative examples A to D each describe the preparation of (cyclo)aliphatic diisocyanates using commercial urea with a formaldehyde content of 0.55% by weight.

EXAMPLE 1

A mixture of 41.0 kg/h of 5-amino-1,3,3-trimethylcyclohexanemethanamine, 29.8 kg/h of unconditioned urea and 107.0 kg/h of n-butanol were pumped via a steam-heated preheater to the first tray of a distillation reactor. The liberated ammonia was continuously removed from the reaction mixture under normal pressure.

The mean residence time in the distillation reactor was 7 h. In the bottom of the distillation reactor operated under standard pressure, 12.5 kg/h of butanol from the bottom of an ammonia-butanol separating column were fed into the bottom of the distillation reactor. The amount of energy supplied to the distillation reactor in the reboiler is regulated such that the amount of butanol which is obtained at the top together with the ammonia formed and is condensed in the dephlegmator with warm water at 40° C. corresponds to that introduced in the bottom. The alcohol thus condensed is conducted continuously into an ammonia-butanol separating column. The solution of bisurea in alcohol obtained in the bottom of the distillation reactor was conducted under level control, via a preheater where it was heated to 190 to 200° C., together with 62.0 kg/h of reaction product from the recarbamatization stage, to the uppermost tray of the pressure distillation reactor. The mean residence time in the pressure distillation reactor was 10.5 h. Heating established the following temperature profile: bottom 229° C. and top 200° C. 103.0 kg/h of butanol were introduced into the bottom of the pressure distillation reactor, and the amount of heat carrier oil to the reboiler was regulated such that the amount of butanol drawn off together with the ammonia formed at the top corresponded to that fed in in the bottom.

The butanol/ammonia mixture obtained was subsequently conducted into the ammonia-butanol separating column. The top temperature there was 85° C. The butanol losses which arose through the ammonia discharge and from other losses (low boiler components and residues sent to incineration) were replaced by supplying 4.7 kg/h of fresh butanol into the bottom of the ammonia-butanol separating column. The mixture of 233.2 kg/h obtained in the bottom of the pressure distillation reactor was purified by distillation.

115.5 kg/h of biscarbamate were fed into the falling film evaporator of the combined cleavage and rectification column after addition of 0.2 kg/h of catalyst solution. The energy required for the cleavage and rectification was transferred with heat carrier oil in the falling film evaporator. The carbamate cleavage reaction was undertaken at a bottom pressure of 27 mbar and a bottom temperature of 230° C. The butanol of 40.0 kg/h which was formed during the cleavage and obtained at the top by rectification was drawn off and fed to the recarbamatization stage with the bottoms discharge of 21.7 kg/h from the combined cleavage and rectification column.

The crude diisocyanate of 55.4 kg/h drawn off in a side stream from the combined cleavage and rectification column was fed to a further purifying distillation so as to obtain 52.0 kg/h of purified diisocyanate. The purity of the diisocyanate obtained was determined by gas chromatography to be >99.5% by weight. The overall process yield based on diamine used was 97.2%.

COMPARATIVE EXAMPLE A

A mixture of 35.7 kg/h of 5-amino-1,3,3-trimethylcyclohexanemethanamine, 25.9 kg/h of conditioned urea with a formaldehyde content of 0.55% by weight and 93.2 kg/h of n-butanol were pumped via a steam-heated preheater to the first tray of a distillation reactor. The liberated ammonia was continuously removed from the reaction mixture under normal pressure.

The mean residence time in the distillation reactor was 7 h. In the bottom of the distillation reactor operated under standard pressure, 11.0 kg/h of butanol from the bottom of an ammonia-butanol separating column were fed into the bottom of the distillation reactor. The amount of energy supplied to the distillation reactor in the reboiler is regulated such that the amount of butanol which is obtained at the top together with the ammonia formed and is condensed in the dephlegmator with warm water at 40° C. corresponds to that introduced in the bottom. The alcohol thus condensed is conducted continuously into an ammonia-butanol separating column. The solution of bisurea in alcohol obtained in the bottom of the distillation reactor was conducted under level control, via a preheater where it was heated to 190 to 200° C., together with 51.2 kg/h of reaction product from the recarbamatization stage, to the uppermost tray of the pressure distillation reactor. The mean residence time in the pressure distillation reactor was 10.5 h. Heating established the following temperature profile: bottom 229° C. and top 200° C. 89.0 kg/h of butanol were introduced into the bottom of the pressure distillation reactor, and the amount of heat carrier oil to the reboiler was regulated such that the amount of butanol drawn off together with the ammonia formed at the top corresponded to that fed in in the bottom.

The butanol/ammonia mixture obtained was subsequently conducted into the ammonia-butanol separating column. The top temperature there was 85° C. The butanol losses which arose through the ammonia discharge and from other losses (low boiler components and residues sent to incineration) were replaced by supplying 4.5 kg/h of fresh butanol into the bottom of the ammonia-butanol separating column. The mixture of 212.1 kg/h obtained in the bottom of the pressure distillation reactor was purified by distillation.

94.1 kg/h of biscarbamate were fed into the falling film evaporator of the combined cleavage and rectification column after addition of 0.2 kg/h of catalyst solution. The energy required for the cleavage and rectification was transferred with heat carrier oil in the falling film evaporator. The carbamate cleavage reaction was undertaken at a bottom pressure of 27 mbar and a bottom temperature of 234° C. The butanol of 33.1 kg/h which was formed during the cleavage and obtained at the top by rectification was drawn off and fed to the recarbamatization stage with the bottoms discharge of 17.9 kg/h from the combined cleavage and rectification column.

The crude diisocyanate of 45.82 kg/h drawn off in a side stream from the combined cleavage and rectification column was fed to a further purifying distillation so as to obtain 43.0 kg/h of purified diisocyanate. The purity of the diisocyanate obtained was determined by gas chromatography to be 98.6% by weight. The overall process yield based on diamine used was 92.3%.

EXAMPLE 2

A mixture of 38.4 kg/h of 5-amino-1,3,3-trimethylcyclohexanemethanamine, 27.9 kg/h of unconditioned urea, 100.1 kg/h of n-butanol and 57.4 kg/h of reaction product from the recarbamatization stage were pumped via a steam-heated preheater, where it was heated to 190 to 200° C., to the first tray of a pressure distillation reactor.

The mean residence time in the pressure distillation reactor was 10.5 h. Heating established the following temperature profile: bottom 230° C. and top 200° C. 96.7 kg/h of butanol were introduced into the bottom of the pressure distillation reactor, and the amount of heat carrier oil to the reboiler was regulated such that the amount of butanol drawn off at the top together with the ammonia formed corresponded to that fed in in the bottom.

The resulting butanol/ammonia mixture was subsequently conducted into the ammonia-butanol separating column. The top temperature there was 87° C. The butanol losses which arose through the ammonia discharge and from other losses (low boiler components and residues sent to incineration) were replaced by supplying 4.7 kg/h of fresh butanol in the bottom of the ammonia-butanol separating column. The mixture of 220.2 kg/h obtained in the bottom of the pressure distillation reactor was purified by distillation.

105.5 kg/h of biscarbamate were fed into the falling film evaporator of the combined cleavage and rectification column after addition of 0.2 kg/h of catalyst solution. The energy required for the cleavage and rectification was transferred with heat carrier oil in the falling film evaporator. The carbamate cleavage reaction was undertaken at a bottom pressure of 27 mbar and a bottom temperature of 230° C. The butanol of 37.1 kg/h which was formed during the cleavage and obtained by rectification at the top was drawn off and fed to the recarbamatization stage with the bottoms discharge of 20.1 kg/h from the combined cleavage and rectification column.

The crude diisocyanate of 51.4 kg/h drawn off in a side stream from the combined cleavage and rectification column was fed to a further purifying distillation, and 48.2 kg/h of purified diisocyanate were thus obtained. The purity of the diisocyanate obtained was determined by gas chromatography to be >99.5% by weight. The overall process yield based on diamine used was 96.3%.

COMPARATIVE EXAMPLE B

A mixture of 35.6 kg/h of 5-amino-1,3,3-trimethylcyclohexanemethanamine, 25.9 kg/h of conditioned urea with a formaldehyde content of 0.55% by weight, 93.0 kg/h of n-butanol and 50.9 kg/h of reaction product from the recarbamatization stage were pumped via a steam-heated preheater, where it was heated to 190 to 200° C., to the first tray of a pressure distillation reactor.

The mean residence time in the pressure distillation reactor was 10.5 h. Heating established the following temperature profile: bottom 232° C. and top 200° C. 88.9 kg/h of butanol were introduced into the bottom of the pressure distillation reactor, and the amount of heat carrier oil to the reboiler was regulated such that the amount of butanol drawn off at the top together with the ammonia formed corresponded to that fed in in the bottom.

The resulting butanol/ammonia mixture was subsequently conducted into the ammonia-butanol separating column. The top temperature there was 88° C. The butanol losses which arose through the ammonia discharge and from other losses (low boiler components and residues sent to incineration) were replaced by supplying 4.6 kg/h of fresh butanol in the bottom of the ammonia-butanol separating column. The mixture of 212.3 kg/h obtained in the bottom of the pressure distillation reactor was purified by distillation.

93.4 kg/h of biscarbamate were fed into the falling film evaporator of the combined cleavage and rectification column after addition of 0.2 kg/h of catalyst solution. The energy required for the cleavage and rectification was transferred with heat carrier oil in the falling film evaporator. The carbamate cleavage reaction was undertaken at a bottom pressure of 27 mbar and a bottom temperature of 234° C. The butanol of 32.8 kg/h which was formed during the cleavage and obtained by rectification at the top was drawn off and fed to the recarbamatization stage with the bottoms discharge of 17.8 kg/h from the combined cleavage and rectification column.

The crude diisocyanate of 45.5 kg/h drawn off in a side stream from the combined cleavage and rectification column was fed to a further purifying distillation, and 42.7 kg/h of purified diisocyanate were thus obtained. The purity of the diisocyanate obtained was determined by gas chromatography to be 98.5% by weight. The overall process yield based on diamine used was 91.9%.

EXAMPLE 3

A mixture of 34.7 kg/h of (2,2,4-)2,4,4-trimethylhexamethylenediamine, 27.2 kg/h of unconditioned urea, 97.8 kg/h of n-butanol and 64.0 kg/h of reaction product from the recarbamatization stage were pumped via a steam-heated preheater, where it was heated to 190 to 200° C., to the first tray of a pressure distillation reactor.

The mean residence time in the pressure distillation reactor was 10.5 h. Heating established the following temperature profile: bottom 228° C. and top 200° C. 94.3 kg/h of butanol were introduced into the bottom of the pressure distillation reactor, and the amount of heat carrier oil to the reboiler was regulated such that the amount of butanol drawn off at the top together with the ammonia formed corresponded to that fed in in the bottom.

The resulting butanol/ammonia mixture was subsequently conducted into the ammonia-butanol separating column. The top temperature there was 86° C. The butanol losses which arose through the ammonia discharge and from other losses (low boiler components and residues sent to incineration) were replaced by supplying 4.5 kg/h of fresh butanol in the bottom of the ammonia-butanol separating column. The mixture of 219.0 kg/h obtained in the bottom of the pressure distillation reactor was purified by distillation.

108.4 kg/h of biscarbamate were fed into the falling film evaporator of the combined cleavage and rectification column after addition of 0.2 kg/h of catalyst solution. The energy required for the cleavage and rectification was transferred with heat carrier oil in the falling film evaporator. The carbamate cleavage reaction was undertaken at a bottom pressure of 27 mbar and a bottom temperature of 228° C. The butanol of 38.1 kg/h which was formed during the cleavage and obtained by rectification at the top was drawn off and fed to the recarbamatization stage with the bottoms discharge of 25.7 kg/h from the combined cleavage and rectification column.

The crude diisocyanate of 47.5 kg/h drawn off in a side stream from the combined cleavage and rectification column was fed to a further purifying distillation, and 44.6 kg/h of purified diisocyanate were thus obtained. The purity of the diisocyanate obtained was determined by gas chromatography to be >99.5% by weight. The overall process yield based on diamine used was 96.6%.

COMPARATIVE EXAMPLE C

A mixture of 34.6 kg/h of (2,2,4-)2,4,4-trimethylhexamethylenediamine, 27.0 kg/h of conditioned urea with a formaldehyde content of 0.55% by weight, 97.3 kg/h of n-butanol and 59.8 kg/h of reaction product from the recarbamatization stage were pumped via a steam-heated preheater, where it was heated to 190 to 200° C., to the first tray of a pressure distillation reactor.

The mean residence time in the pressure distillation reactor was 10.5 h. Heating established the following temperature profile: bottom 231° C. and top 200° C. 93.1 kg/h of butanol were introduced into the bottom of the pressure distillation reactor, and the amount of heat carrier oil to the reboiler was regulated such that the amount of butanol drawn off at the top together with the ammonia formed corresponded to that fed in in the bottom.

The resulting butanol/ammonia mixture was subsequently conducted into the ammonia-butanol separating column. The top temperature there was 89° C. The butanol losses which arose through the ammonia discharge and from other losses (low boiler components and residues sent to incineration) were replaced by supplying 5.1 kg/h of fresh butanol in the bottom of the ammonia-butanol separating column. The mixture of 228.1 kg/h obtained in the bottom of the pressure distillation reactor was purified by distillation. 101.3 kg/h of biscarbamate were fed into the falling film evaporator of the combined cleavage and rectification column after addition of 0.2 kg/h of catalyst solution. The energy required for the cleavage and rectification was transferred with heat carrier oil in the falling film evaporator. The carbamate cleavage reaction was undertaken at a bottom pressure of 27 mbar and a bottom temperature of 233° C. The butanol of 35.6 kg/h which was formed during the cleavage and obtained by rectification at the top was drawn off and fed to the recarbamatization stage with the bottoms discharge of 24.0 kg/h from the combined cleavage and rectification column. The crude diisocyanate of 44.4 kg/h drawn off in a side stream from the combined cleavage and rectification column was fed to a further purifying distillation, and 41.7 kg/h of purified diisocyanate were thus obtained. The purity of the diisocyanate obtained was determined by gas chromatography to be 98.2% by weight. The overall process yield based on diamine used was 90.8%.

EXAMPLE 4

The uppermost tray of a pressure distillation reactor was charged with 31.9 kg/h of $H_{12}$MDA, 18.7 kg/h of unconditioned urea and 67.4 kg/h of n-butanol, and the reaction mixture was converted with continuous removal of the ammonia released at 10 bar, 220° C. and with a mean residence time of 10.5 h. In the bottom of the pressure distillation reactor, 66.1 kg/h of butanol were fed in, and the amount of alcohol drawn off at the top together with the ammonia released was selected such that it corresponded to the alcohol input in the bottom. The resulting butanol/ammonia mixture was subsequently conducted into the ammonia-butanol separating column. The top temperature there was 86° C. The butanol losses which arose through the ammonia discharge and from other losses (low boiler components and residues sent to incineration) were replaced by supply of fresh butanol in the bottom of the ammonia-butanol separating column. The reactor discharge, together with the material of value stream from the high boiler removal, was freed by distillation of excess butanol and low and medium boilers, and the remaining 89.9 kg/h of bis(4-butoxycarbonylaminocyclohexyl)methane ($H_{12}$MDU) were conducted as a melt (140° C.) into the circulation system of the falling film evaporator of the cleavage and rectification column, and the deblocking reaction was performed at a temperature of 234° C. and a bottom pressure of 8 mbar in the presence of a catalyst. The crude $H_{12}$MDI obtained was fed to a purifying distillation to obtain 37.3 kg/h of pure $H_{12}$MDI. 26.3 kg/h of crude butanol were obtained as the top product of the cleavage and rectification column. To maintain constant mass within the cleavage and rectification column, and prevent deposits and blockages of the cleavage apparatus, a substream was discharged continuously from the circulation system and combined with 2.2 kg/h of bottoms discharge from the $H_{12}$MDI purifying distillation and the top product from the cleavage and rectification column and reurethanized. The reurethanized stream was freed of excess butanol and separated by distillation into a waste stream rich in high boilers and a material of value stream. The 28.8 kg/h of material of value stream were fed together with the reactor effluent of the diurethane preparation to the flash stage. The purity of the diisocyanate obtained was determined by gas chromatography to be >99.5% by weight. The overall process yield based on diamine used was 93.8%.

COMPARATIVE EXAMPLE D

The uppermost tray of a pressure distillation reactor was charged with 29.9 kg/h of $H_{12}$MDA, 17.6 kg/h of conditioned urea with a formaldehyde content of 0.55% by weight and 63.3 kg/h of n-butanol, and the reaction mixture was converted with continuous removal of the ammonia released at 10 bar, 220° C. and with a mean residence time of 10.5 h. In the bottom of the pressure distillation reactor, 63.2 kg/h of butanol were fed in, and the amount of alcohol drawn off at the top together with the ammonia released was selected such that it corresponded to the alcohol input in the bottom. The resulting butanol/ammonia mixture was subsequently conducted into the ammonia-butanol separating column. The top temperature there was 88° C. The butanol losses which arose through the ammonia discharge and from other losses (low boiler components and residues sent to incineration) were replaced by supply of fresh butanol in the bottom of the ammonia-butanol separating column. The reactor discharge, together with the material of value stream from the high boiler removal, was freed by distillation of excess butanol and low and medium boilers, and the remaining 78.6 kg/h of bis(4-butoxycarbonylaminocyclohexyl)methane ($H_{12}$MDU) were conducted as a melt (140° C.) into the circulation system of the falling film evaporator of the cleavage and rectification column, and the deblocking reaction was performed at a temperature of 240° C. and a bottom pressure of 11 mbar in the presence of a catalyst. The crude $H_{12}$MDI obtained was fed to a purifying distillation to obtain 32.6 kg/h of pure $H_{12}$MDI. 23.0 kg/h of crude butanol were obtained as the top product of the cleavage and rectification column. To maintain constant mass within the cleavage and rectification column, and prevent deposits and blockages of the cleavage apparatus, a substream was discharged continuously from the circulation system and combined with 2.0 kg/h of bottoms discharge from the $H_{12}MDI$ purifying distillation and the top product from the cleavage and rectification column and reurethanized. The reurethanized stream was freed of excess butanol and separated by distillation into a waste stream rich in high boilers and a material of value stream. The 21.1 kg/h of material of value stream were fed together with the reactor effluent of the diurethane preparation to the flash stage. The purity of the diisocyanate obtained was determined by gas chromatography to be 98.0% by weight. The overall process yield based on diamine used was 87.3%.

Table 1 which follows shows once again, in summary, the essential features of examples 1 to 8 with the significant differences in the diisocyanate purities and the process yields depending on the urea quality used.

TABLE 1

| Name | Dimension | Example 1 | A | 2 | B | 3 | C | 4 | D |
|---|---|---|---|---|---|---|---|---|---|
| Diamine | kg/h | IPD 41 | IPD 35.7 | IPD 38.4 | IPD 35.6 | TMD 34.7 | TMD 34.6 | $H_{12}MDA$ 31.9 | $H_{12}MDA$ 29.9 |
| Urea with <10 ppm of formaldehyde | kg/h | 29.8 | 0 | 27.9 | 0 | 27.2 | 0 | 18.7 | 0 |
| Urea with 0.55% by wt. of formaldehyde | kg/h | 0 | 25.9 | 0 | 25.9 | 0 | 27.0 | 0 | 17.6 |
| Diisocyanate | kg/h | 52.0 | 43.0 | 48.2 | 42.7 | 44.6 | 41.7 | 37.3 | 32.6 |
| Diisocyanate purity | % by wt. | >99.5 | 98.6 | >99.5 | 98.5 | >99.5 | 98.2 | >99.5 | 98.0 |
| Process yield | % | 97.2 | 92.3 | 96.3 | 91.9 | 96.6 | 90.8 | 93.8 | 87.3 |

IPD: 5-Amino-1,3,3-trimethylcyclohexanemethanamine
TMD: (2,2,4-)2,4,4-Trimethylhexamethylenediamine
$H_{12}MDA$: Mixture of isomeric methylenedicyclohexyldiamine
The diisocyanate purities were determined by gas chromatography:
Instrument: HP3/Agilent GC 6890
Separating column: HP5/Agilent 30 m × 320 μm × 0.25 μm nominal
The process yield is calculated from diisocyanate obtained based on diamine used.

The invention claimed is:

1. A process for continuously preparing (cyclo)aliphatic diisocyanates without removing by-products generated from impurities present in conditioned urea; consisting essentially of:
   (1) reacting at least one (cyclo)aliphatic diamine with unconditioned urea, an unconditioned urea equivalent, or a combination thereof, and at least one alcohol to give (cyclo)aliphatic biscarbamates; and
   (2) subsequently thermally cleaving the (cyclo)aliphatic biscarbamates to (cyclo)aliphatic diisocyanates,
   wherein unconditioned urea and an unconditioned urea equivalent mean urea and an urea equivalent which have not been surface treated with inorganic substances, have not been surface treated by formaldehyde or a formaldehyde-containing component, and have not been melt treated by the addition of formaldehyde or a formaldehyde-containing component to a urea melt;
   wherein the process yield utilizing unconditioned urea, unconditioned urea equivalent, or a combination thereof calculated based on (cyclo)aliphatic diamine used is a minimum of 4.8% greater than the process yield utilizing conditioned urea, a conditioned urea equivalent, or a combination thereof.

2. A multistage process for continuously preparing (cyclo)aliphatic diisocyanates without removing by-products generated from impurities present in conditioned urea; consisting essentially of:
   (1) reacting at least one (cyclo)aliphatic diamine with unconditioned urea, an unconditioned urea equivalent, or a combination thereof, and at least one alcohol to give (cyclo)aliphatic biscarbamates; and
   (2) subsequently thermally cleaving the (cyclo)aliphatic biscarbamates to (cyclo)aliphatic diisocyanates,
   wherein the (cyclo)aliphatic biscarbamates are formed by one-stage, two-stage or multistage processes and wherein unconditioned urea and an unconditioned urea equivalent mean urea and an urea equivalent which have not been surface treated with inorganic substances, have not been surface treated by formaldehyde or a formaldehyde-containing component, and have not been melt treated by the addition of formaldehyde or a formaldehyde-containing component to a urea melt;
   wherein the process yield utilizing unconditioned urea, unconditioned urea equivalent, or a combination thereof calculated based on (cyclo)aliphatic diamine used is a minimum of 4.8% greater than the process yield utilizing conditioned urea, a conditioned urea equivalent, or a combination thereof.

3. The process according to claim 1, wherein
   the (cyclo)aliphatic diisocyanate product has a purity greater than 99.5% by weight.

4. The process according to claim 3, wherein
   the unconditioned urea does not contain talc, bentonites, kieselguhr, diatoms, kaolin or other silicatic substances.

5. The process according to claim 1,
   wherein the at least one alcohol is selected from the group consisting of methanol, ethanol, 1-propanol, 1-butanol, 2-butanol, 1-hexanol, and cyclohexanol.

6. The process according to claim 1 for preparing isophorone diisocyanate.

7. The process according to claim 1, wherein
   the maximum formaldehyde concentration of the urea present is 0.001 to 0.01% by weight.

8. The process according to claim 2, wherein
   the (cyclo)aliphatic diisocyanate product has a purity greater than 99.5% by weight.

9. The process according to claim 8, wherein
   the unconditioned urea does not contain talc, bentonites, kieselguhr, diatoms, kaolin or other silicatic substances.

10. The process according to claim 2, wherein
   the at least one alcohol is selected from the group consisting of methanol, ethanol, 1-propanol, 1-butanol, 2-butanol, 1-hexanol, and cyclohexanol.

11. The process according to claim 2 for preparing isophorone diisocyanate.

12. The process according to claim 2, wherein the maximum formaldehyde concentration of the urea present is 0.001 to 0.01% by weight.

13. The process according to claim 3,
wherein the process yield utilizing unconditioned urea, unconditioned urea equivalent, or a combination thereof calculated based on (cyclo)aliphatic diamine used is 4.8 to 7.4% greater than the process yield utilizing conditioned urea, a conditioned urea equivalent, or a combination thereof; and
wherein the purity of the (cyclo)aliphatic diisocyanate product prepared utilizing unconditioned urea, unconditioned urea equivalent, or a combination thereof is improved by no more than 1.5% over the (cyclo)aliphatic diisocyanate product prepared utilizing conditioned urea, a conditioned urea equivalent, or a combination thereof.

14. The process according to claim 8,
wherein the process yield utilizing unconditioned urea, unconditioned urea equivalent, or a combination thereof calculated based on (cyclo)aliphatic diamine used is 4.8 to 7.4% greater than the process yield utilizing conditioned urea, a conditioned urea equivalent, or a combination thereof; and
wherein the purity of the (cyclo)aliphatic diisocyanate product prepared utilizing unconditioned urea, unconditioned urea equivalent, or a combination thereof is improved by no more than 1.5% over the (cyclo)aliphatic diisocyanate product prepared utilizing conditioned urea, a conditioned urea equivalent, or a combination thereof.

* * * * *